US008480744B2

(12) United States Patent
Li et al.

(10) Patent No.: US 8,480,744 B2
(45) Date of Patent: *Jul. 9, 2013

(54) METHOD OF PREPARING AN IMPLANT FOR DELIVERY INTO A VERTEBRAL SPACE

(75) Inventors: Lehmann K. Li, Milford, CT (US); Rhodemann Li, Darien, CT (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1805 days.

This patent is subject to a terminal disclaimer.

(21) Appl. No.: 11/486,622

(22) Filed: Jul. 14, 2006

(65) Prior Publication Data

US 2006/0253122 A1  Nov. 9, 2006

Related U.S. Application Data (63) Continuation of application No. 10/317,632, filed on Dec. 12, 2002, now Pat. No. 7,081,120, which is a continuation-in-part of application No. 09/998,978, filed on Nov. 15, 2001, now Pat. No. 6,733,505, which is a continuation-in-part of application No. 09/559,899, filed on Apr. 26, 2000, now Pat. No. 6,764,514.

(60) Provisional application No. 60/341,343, filed on Dec. 13, 2001, provisional application No. 60/248,807, filed on Nov. 15, 2000, provisional application No. 60/131,053, filed on Apr. 26, 1999.

(51) Int. Cl.
*A61F 2/44* (2006.01)
(52) U.S. Cl.
USPC .......................................... 623/17.16; 623/923
(58) Field of Classification Search
USPC .............. 606/107, 86 A, 99, 914; 623/17.16, 623/902, 907–909, 911, 923
See application file for complete search history.

(56) References Cited

U.S. PATENT DOCUMENTS

| 3,875,595 | A | 4/1975 | Froning |
| 4,157,085 | A | 6/1979 | Austad |
| 4,573,998 | A | 3/1986 | Mazzocco |
| 5,005,591 | A | 4/1991 | Austad |
| 5,171,280 | A | 12/1992 | Baumgartner |
| 5,534,028 | A | 7/1996 | Bao et al. |
| 5,562,736 | A | 10/1996 | Ray et al. |
| 5,674,295 | A | 10/1997 | Ray et al. |
| 5,674,296 | A | 10/1997 | Bryan et al. |
| 5,702,454 | A * | 12/1997 | Baumgartner ................ 623/908 |
| 5,711,317 | A | 1/1998 | McDonald |
| 5,873,879 | A * | 2/1999 | Figueroa et al. .............. 606/107 |
| 6,132,465 | A | 10/2000 | Ray et al. |
| 6,280,449 | B1 | 8/2001 | Blake |
| 6,402,785 | B1 | 6/2002 | Zdeblick et al. |
| 6,733,505 | B2 * | 5/2004 | Li ................................. 623/923 |
| 7,081,120 | B2 * | 7/2006 | Li et al. ........................... 606/99 |
| 2003/0125748 | A1 | 7/2003 | Li et al. |

* cited by examiner

FOREIGN PATENT DOCUMENTS

WO  WO 00/64385 A1  11/2000

*Primary Examiner* — Brian E. Pellegrino (57) ABSTRACT

A method for delivering a spinal implant into a vertebral space, including providing a spinal implant, providing a die member defining an opening sized to receive the implant while in an initial configuration, inserting the implant into the opening in the die member, displacing the implant relative to the die member, transitioning the implant from the initial configuration to a deformed configuration having a reduced lateral profile relative to the initial configuration, and discharging the implant from the die member and inserting the implant into the vertebral space while in the deformed configuration.

19 Claims, 8 Drawing Sheets

METHOD OF PREPARING AN IMPLANT FOR DELIVERY INTO A VERTEBRAL SPACE

CROSS REFERENCE TO RELATED APPLICATIONS

The present application is a continuation of U.S. patent application Ser. No. 10/317,632, filed on Dec. 12, 2002, now U.S. Pat. No. 7,081,120 which claims the benefit of U.S. Provisional Application Ser. No. 60/341,343, filed Dec. 13, 2001, and is a continuation-in-part application of U.S. patent application Ser. No. 09/998,978, filed Nov. 15, 2001 and issued as U.S. Pat. No. 6,733,505, which claims the benefit of U.S. Provisional Application Ser. No. 60/248,807, filed Nov. 15, 2000, and is also a continuation-in-part application of U.S. patent application Ser. No. 09/559,899, filed Apr. 26, 2000 and issued as U.S. Pat. No. 6,764,514, which claims the benefit of U.S. Provisional Application Ser. No. 60/131,053, filed Apr. 26, 1999, the contents of each application hereby being incorporated by reference in their entirety.

FIELD OF THE INVENTION

The present invention relates generally to the field of surgical instrumentation and methods for treatment of the spine, and more particularly relates to instrumentation and methods for delivering an implant into a vertebral space.

BACKGROUND

The spinal column is a flexible chain of closely linked vertebral bodies. In a normal human spine, there are seven cervical, twelve thoracic and five lumbar vertebrae. Below the lumbar vertebrae are the sacrum and coccyx. Each individual vertebral body has an outer shell of hard, dense bone. Inside the vertebral body is a honeycomb of cancellous bone containing red bone marrow. All of the red blood cells, and many of the white blood cells, are generated inside the cancellous bone where the blood cells mature before being released into the blood stream.

The intervertebral disc, also known as the spinal disc, serves as a cushion between adjacent vertebral bodies so as to permit controlled motion therebetween. A healthy intervertebral disc consists of three components: a gelatinous inner core (the nucleus pulposus), a series of overlapping and laminated plies of tough fibrous rings (the annulus fibrosus), and superior and inferior thin cartilage layers connecting the intervertebral disc to the thin cortical bone of the adjacent vertebral bodies (the vertebtral end plates).

An intervertebral disc may be displaced and/or damaged due to trauma (e.g., a herniated disc) or by disease (e.g., a degenerative disc disease). A herniated disc may bulge out and compress itself onto a nerve, thereby resulting in lower leg pain, loss of muscle control or paralysis. To treat a herniated disc, the offending portions of the disc, which typically includes a bulging portion of the nucleus pulposus, are removed via well-known surgical procedures. A degenerative disc disease typically causes the intervertebral disc to gradually reduce in height, thereby causing the annulus fibrosus to buckle, tear or separate in a radial and/or circumferential direction, commonly resulting in persistent and disabling back pain. Degenerative disc disease may be treated by surgically removing the nucleus pulposus and fusing the adjacent vertebral bodies to stabilize the joint. In either case, whether removing some or all of the nucleus pulposus, these procedures place greater stress on adjacent intervertebral discs to compensate for lost motion capabilities which may in turn cause premature degeneration of the adjacent intervertebral discs.

One drawback of current prosthetic disc implants is that the annulus fibrosis and/or other portions of the intervertebral disc are weakened by either large or multiple incisions and/or cut outs that are required in order to insert the prosthetic disc implant into the intervertebral space between adjacent vertebrae. Additionally, incisions or cut outs in the annulus fibrosis are not easily repaired, thereby increasing the risk that the prosthetic disc implant may eventually work its way out of the intervertebral space and possibly interfere with or damage adjacent anatomical tissue. A further deficiency of current prosthetic disc implants is that multiple laterally spaced prosthetic implants are sometimes required to be inserted within the intervertebral space, thereby requiring careful and precise positioning of the prosthetic implants to ensure proper load carrying characteristics. (See, e.g., U.S. Pat. No. 5,674,295 to Ray et al.).

Modern trends in surgery are directed toward restoration of bodily function and/or form (i.e., repair) of anatomical structures through the use of minimally invasive surgical techniques. The ability to surgically repair damaged tissues or joints via the creation of a minimal number of incisions and as small incisions as possible produces less trauma and pain for the patient while generally yielding better clinical outcomes.

Thus, there is a general need in the industry to provide improved instrumentation and methods for delivering an implant into a vertebral space, preferably in a minimally invasive manner. The present invention meets this need and provides other benefits and advantages in a novel and unobvious manner.

SUMMARY

The present invention relates generally to instrumentation and methods for delivering an implant to a vertebral space. While the actual nature of the invention covered herein can only be determined with reference to the claims appended hereto, certain forms of the invention that are characteristic of the preferred embodiments disclosed herein are described briefly as follows.

It is one object of the present invention to provide improved instrumentation and methods for delivering an implant into a vertebral space.

Further objects, features, advantages, benefits, and aspects of the present invention will become apparent from the drawings and description contained herein.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Figure 1:
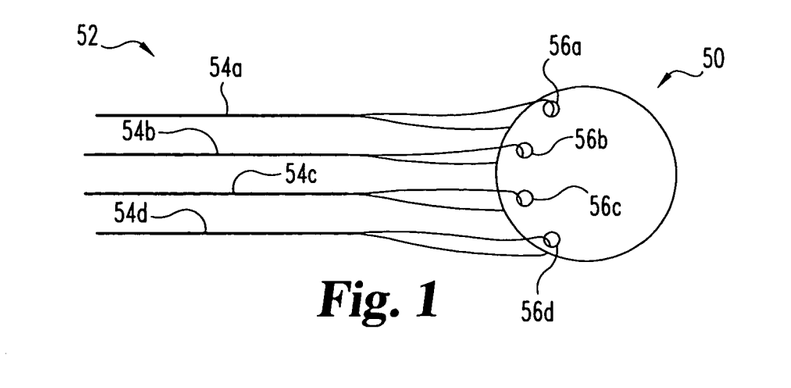
FIG. 1 is a top plan view of an implant according to one form of the present invention.

Referring to FIG. 1, shown therein is an implant 50 according to one form of the present invention. In one embodiment of the invention, the implant 50 is a spinal implant suitable for insertion into a vertebral space. In a specific embodiment, the implant 50 is a prosthetic nucleus suitable for insertion into an intervertebral disc space to replace at least a portion of the nucleus pulposus of a natural intervertebral disc. It should be understood, however, that the implant 50 may be configured to replace other portions of the spine and may also be used in association with portions of the anatomy other than the spine.

In one aspect of the present invention, the prosthetic nucleus 50 is capable of being transitioned from an initial, relatively flat, disc-like configuration (FIG. 1) to a more compact, folded configuration (FIG. 6) and reformed back toward the initial disc-like configuration upon insertion of the prosthetic nucleus 50 into a vertebral space. The prosthetic nucleus 50 is preferably formed of a material that is relatively elastic so as to facilitate deformation between the initial disc-like configuration and the folded configuration and reformation back toward the initial configuration In one embodiment of the invention, a force applying means 52 extends from the prosthetic nucleus 50 and serves to draw the prosthetic nucleus 50 through a delivery instrument, the details of which will be discussed below. In one embodiment, the force applying means 52 comprises one or more filaments or strands 54a-54d. In a further embodiment, the filaments 54a-54d comprise sutures. In a specific embodiment, the sutures 54a-54d are inserted through apertures 56a-56d, respectively, extending through the prosthetic nucleus 50 to thereby form a corresponding number of suture loops. In this manner, the sutures 54a-54d may be removed from the prosthetic nucleus 50 by simply cutting one side of the suture loop and pulling the severed portion of the suture loop through the corresponding aperture 56a-56d. It should be understood, however, that other types and configurations of force applying means 52 are also contemplated as falling within the scope of the present invention, such as, for example, a pushing mechanism or rod adapted to push the prosthetic nucleus 50 through a delivery instrument.

Figure 2:
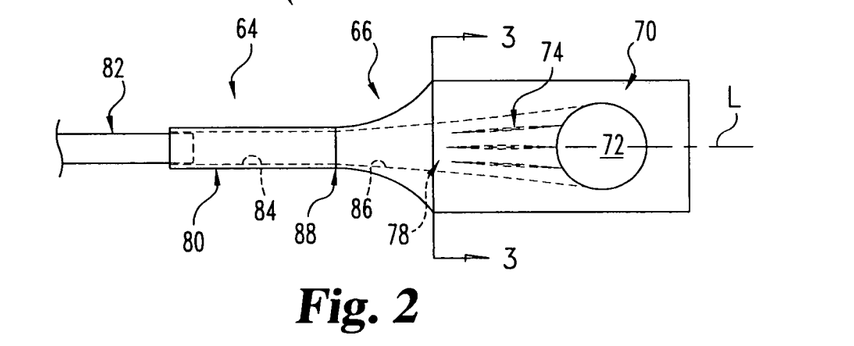
FIG. 2 is a top plan view of an instrument according to one form of the present invention for delivering the implant illustrated in FIG. 1 into a vertebral space.
Figure 3:
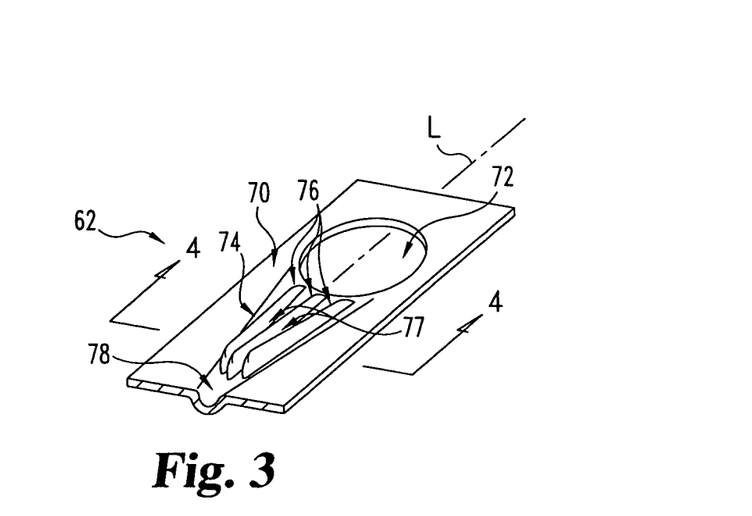
FIG. 3 is a cross-sectional perspective view of the instrument illustrated in FIG. 2, as taken along line 3-3 of FIG. 2.
Figure 4:
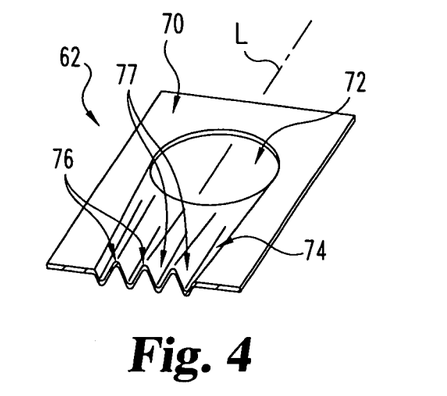
FIG. 4 is a cross-sectional perspective view of the instrument illustrated in FIG. 3, as taken along line 4-4 of FIG. 3.

Referring to FIGS. 2-4, shown therein is a delivery instrument 60 according to one form of the invention for delivering the prosthetic nucleus 50 into a vertebral space. In one embodiment of the invention, the instrument 60 extends along a longitudinal axis L and generally includes a folding portion 62 and an insertion portion 64. In a further embodiment of the invention, the folding portion 62 is releasably coupled to the insertion portion 64 by connection means 66 so as to allow the folding portion 62 to be selectively detached from the insertion portion 64.

In one embodiment of the invention, the folding portion 62 comprises a folding die 70. For purposes of clarity, FIGS. 3-4 illustrate half of the folding die 70, it being understood that the complete folding die 70 includes a similarly configured opposing half (not shown) cooperating with illustrated half to form the folding portion 62. In one embodiment, each half of the folding die 70 has a plate-like configuration and defines a cavity 72 and a number of folding elements 74. The cavity 72 is sized and shaped to receive the prosthetic nucleus 50 therein while the prosthetic nucleus 50 is in its initial configuration. In one embodiment, the cavity 72 has a substantially circular cross-section corresponding to the size and shape of the initial disc-like configuration of the prosthetic nucleus 50. However, the cavity 72 may define other cross-sections, such as, for example, oblong, elliptical, rectangular or polygonal cross-sections.

As illustrated in FIGS. 3 and 4, in one embodiment of the invention, the folding elements 74 are comprised of a number of folding guides 76 and a number of folding grooves or notches 77. The folding guides 76 and grooves 77 extend generally along the longitudinal axis L between the cavity 72 and the connection means 66 and act to initiate the process of reducing the cross-sectional dimensions of the prosthetic nucleus 50 from the initial disc-like configuration (FIG. 1) toward the reduced-profile folded configuration (FIG. 6) to accommodate loading of the prosthetic nucleus 50 into the insertion portion 64 of the delivery instrument 60. In one embodiment, the folding die 70 transitions the prosthetic implant 50 from a relatively flat initial configuration to a substantially cylindrical folded configuration. The folding guides 76 and grooves 77 are inwardly tapered from the cavity 72 toward the connection means 66 to facilitate transitioning of the prosthetic nucleus 50 toward the deformed configuration, gradually transitioning into a delivery portion 78 adjacent the connection means 66 having a substantially cylindrical cross-section.

Figure 6:
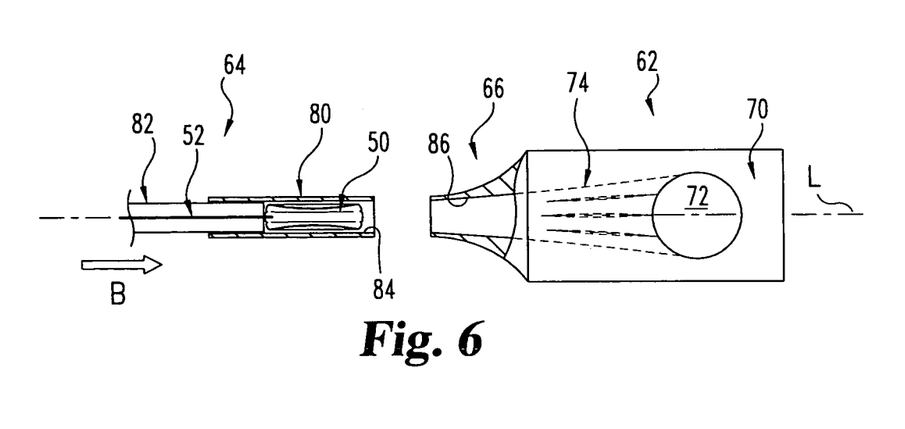
FIG. 6 is a top plan view of the instrument illustrated in FIG. 2, with the implant illustrated in FIG. 1 disposed within a cannula portion of the instrument in a folded configuration.

In one embodiment of the invention, the insertion portion 64 generally comprises a cannula tube 80 and a discharge rod or plunger 82 at least partially disposed within the cannula tube 80. The cannula tube 80 extends generally along the longitudinal axis L and defines a cavity 84 sized and shaped to receive the prosthetic nucleus 50 therein while in the reduced-profile folded configuration (FIG. 6). In one embodiment, the discharge rod 82 is axially displaceable relative to the cannula tube 80 in the direction of arrow B (FIG. 6) to discharge the prosthetic nucleus 50 from the cavity 84 and into a vertebral space.

As discussed above, the folding portion 62 of the delivery instrument 60 is releasably coupled to the insertion portion 64 by a connection means 66 so as to allow the folding portion 62 to be selectively detached from the insertion portion 64 subsequent to the loading of the prosthetic nucleus 50 into the cavity 84 of the insertion portion 64. In the illustrated embodiment of the invention, the connection means 66 defines a passage 86 communicating between the delivery portion 78 of the folding portion 62 and the cavity 84 of the insertion portion 64 to allow the prosthetic nucleus 50 to be transferred therebetween.

In one embodiment of the invention, the connection means 66 comprises a frangible region 88 configured to allow the folding portion 62 to be selectively broken away and separated from the insertion portion 64. In a specific embodiment, the frangible region 88 comprises a region of reduced strength, such as, for example, a region of reduced wall thickness. It should be understood, however, that other types and configurations of connection means 66 are also contemplated. For example, in another embodiment, the connection means 66 may comprise a slidable connection, such as a tongue and groove connection, whereby the folding portion 62 is displaced relative to the insertion portion 64 to selectively detach the folding portion 62 from the insertion portion 64. In a further embodiment, the connection means 66 may be comprised of a threaded connection whereby the folding portion 62 is threadingly coupled to the insertion portion 64 to provide selective detachment therebetween.

Figure 5:
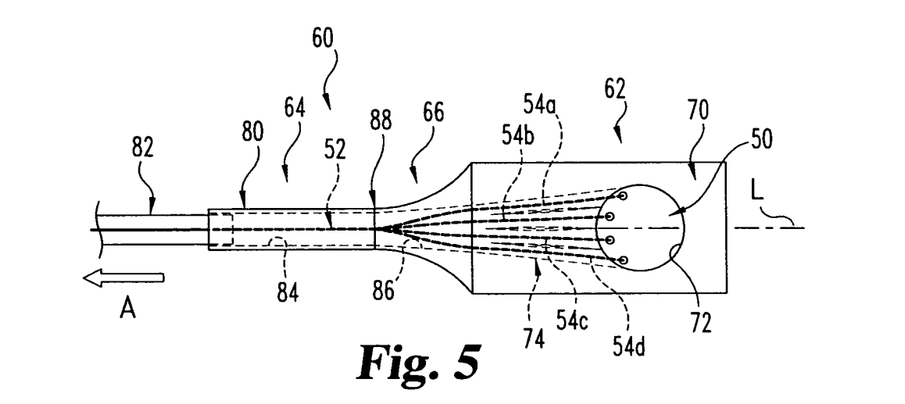
FIG. 5 is a top plan view of the instrument illustrated in FIG. 2, with the implant illustrated in FIG. 1 inserted therein in an initial disc-like configuration.

Referring to FIG. 5, the prosthetic nucleus 50 is initially positioned within the cavity 72 of the folding die 70 while in the substantially flat, disc-like configuration, with the filaments or sutures 54a-54d extending along respective ones of the folding guides 76 and grooves 77 and through the cavity 84 in the cannula tube 80. The filaments 54a-54d are pulled in the direction of arrow A which in turn exerts an axial pulling force onto the prosthetic nucleus 50 to draw the prosthetic nucleus 50 across the folding elements 74 of the folding die 70, thereby resulting in the transitioning of the prosthetic nucleus 50 into a folded configuration having a reduced lateral profile relative (FIG. 6) to the initial disc-like configuration (FIG. 1). The prosthetic nucleus 50 is further drawn through the passage 86 in the connection means 66 and into the distal end portion of the cavity 84 in the cannula tube 80. As discussed above, the filaments or sutures 54a-54d may be disconnected from the prosthetic nucleus 50 by simply cutting one side of the suture loop and pulling the severed portion of the suture loop through the corresponding aperture 56a-56d in the prosthetic nucleus 50. It should be appreciated that the sutures 54a-54d may be removed after the prosthetic nucleus 50 is loaded into the cannula cavity 84 or subsequent to delivery of the prosthetic nucleus 50 into the vertebral space.

Although the illustrated embodiment of the invention utilizes filaments or strands 54a-54d as the force applying means 52 to draw the prosthetic nucleus 50 across the folding elements 74 of the folding die 70 and into the cavity 84 of the cannula tube 80, it should be understood that other types and configurations of force applying means 52 are also contemplated. For example, the force applying means 52 may be configured to displace the prosthetic nucleus 50 across the folding elements 74 and into the cavity 84 via a pushing force and/or a rotating force. Additionally, it should be appreciated that the folding elements 74 may take on other shapes and configurations to transition the prosthetic nucleus into other types of deformed configurations. For example, the folding elements 74 may alternatively be configured to curl and/or roll the prosthetic nucleus 50 into a deformed configuration having a reduced lateral profile relative to the initial disc-like configuration. It should also be appreciated that the folding elements 74 need not necessarily be entirely defined by the folding die 70, but may also extend along the passage 86 in the connection means 66 and into the cavity 84 in the cannula tube 80.

Referring now to FIG. 6, once the prosthetic nucleus 50 is folded into the reduced-profile configuration and loaded into the cannula cavity 84, the folding portion 62 of the delivery instrument 60 is selectively detached from the insertion portion 64 via the connection means 66. As discussed above, in the illustrated embodiment of the invention, the connection means 66 includes a frangible region 88 that is configured to allow the folding portion 62 to be snapped off or broken away from the insertion portion 64, thereby providing the cannula tube 80 with an open distal end for unobstructed insertion into the vertebral space. The distal end portion of the cannula tube 80 may then be positioned within a vertebral space in a minimally invasive manner via insertion through a relatively small access portal or opening sized slightly larger than the outer cross-section of the cannula tube 80. The discharge rod 82 is then axially displaced along the cannula cavity 84 in the direction of arrow B and into engagement with the prosthetic nucleus 50. Further displacement of the discharge rod 82 in the direction of arrow B discharges the prosthetic nucleus 50 from the cannula tube 80 and into the vertebral space. After the prosthetic nucleus 50 is discharged from the cannula tube 80 and positioned within the vertebral space, the prosthetic nucleus 50 will begin to reform or unfold back toward the initial disc-like configuration.

Figure 7:
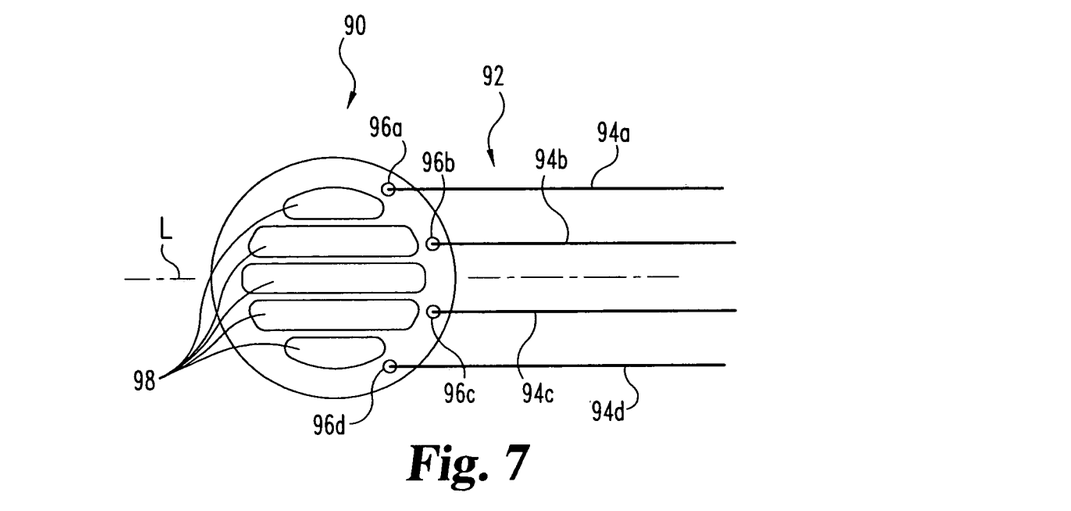
FIG. 7 is an implant according to another embodiment of the present invention.
Figure 8:
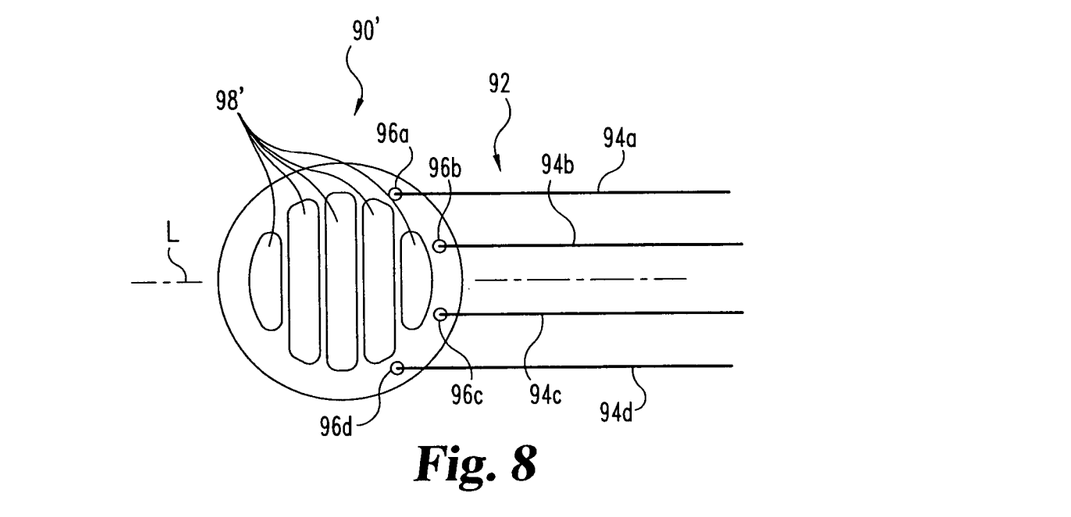
FIG. 8 is an implant according to a further embodiment of the present invention.

Referring to FIGS. 7 and 8, shown therein are additional embodiments of prosthetic nuclei 90 and 90', respectively, which may be used in association with the delivery instrument 60. The prosthetic nuclei 90 and 90' are configured similar to the prosthetic nucleus 50. More specifically, the prosthetic nuclei 90 and 90' each have an initial disc-like configuration that is capable of being transitioned to a more compact, folded configuration, and reformed back toward the initial configuration upon insertion of the prosthetic nucleus into a vertebral space. Additionally, a force applying means 92 extends from each of the prosthetic nuclei 90 and 90' to facilitate displacement of the prosthetic nucleus through the delivery instrument 60. In one embodiment, the force applying means 92 comprises one or more filaments or strands 94a-94d. In a specific embodiment, the filaments 54a-54d comprise sutures which are inserted through apertures 96a-96d, respectively, extending through the prosthetic nuclei 90 and 90' to thereby form a corresponding number of suture loops. It should be understood, however, that other types and configurations of force applying means 92 are also contemplated as falling within the scope of the present invention.

The prosthetic nuclei 90 and 90' each include features that function to permit, assist, facilitate, direct, aid in, and/or control the deformation and/or reformation of the prosthetic nuclei 90 and 90'. As shown in FIG. 7, in one embodiment of the invention, the prosthetic nucleus 90 includes a number of ribbed sections 98 oriented generally parallel with the filaments 94a-94d and/or the longitudinal axis L of the delivery instrument 60. As shown in FIG. 8, in another embodiment of the invention, the prosthetic nucleus 90' includes a number of ribbed sections 98' oriented generally perpendicular to the filaments 94a-94d and/or the longitudinal axis L of the delivery instrument 60. In other embodiments of the invention, the prosthetic nuclei 90 and 90' may include a combination of the ribbed sections 98 and 98'.

Although the illustrated embodiments of the prosthetic nuclei 50, 90 and 90' have a generally flat, disc-like configuration while in the initial configuration (FIGS. 1, 7 and 8), it should be understood that other shapes and configurations are also contemplated. In other embodiments of the invention, the prosthetic nuclei 50, 90 and 90' may include a number of internal or external surfaces (e.g., walls, barriers, supports, etc.) that may be interconnected to provide the prosthetic nuclei with an added degree of strength and/or stability. Additionally, one or more portions of such surfaces may be reinforced or made more rigid to facilitate expansion or to direct expansion in a predetermined direction and/or orientation so as to provide the prosthetic nuclei 50, 90 and 90' with a particular size and/or shape. Once the prosthetic nuclei 50, 90 and 90' are positioned within the intervertebral disc space, the prosthetic nuclei may be configured to change shape due to swelling, hydration, expansion, reaction or by other means, the details of which are disclosed in U.S. patent application Ser. No. 09/559,899, filed Apr. 26, 2000, the contents of which have been incorporated herein by reference.

Although the illustrated embodiments of the prosthetic nuclei 50, 90 and 90' have a unitary, single-piece construct, in other embodiments of the invention, the prosthetic nuclei may be include one or more additional members or elements that are incorporated into, encased within, or attached to the remainder of the implant. For example, such additional members or elements may comprise a material having a weave pattern, or may comprise a material that is configured to permit, assist, facilitate, direct, aid in, and/or control the deformation and/or reformation of the prosthetic nuclei 50, 90 and 90' in a predetermined direction and/or orientation so as to provide the implant with a particular size and/or shape. In another embodiment of the invention, the prosthetic nuclei 50, 90 and 90' may comprise an outer member into which another member is placed, either prior to or subsequent to delivery of the implant into the vertebral space. Alternatively, the prosthetic nuclei 50, 90 and 90' may be placed into another member, either prior to or subsequent to delivery of the implant into the vertebral space.

Figure 9:
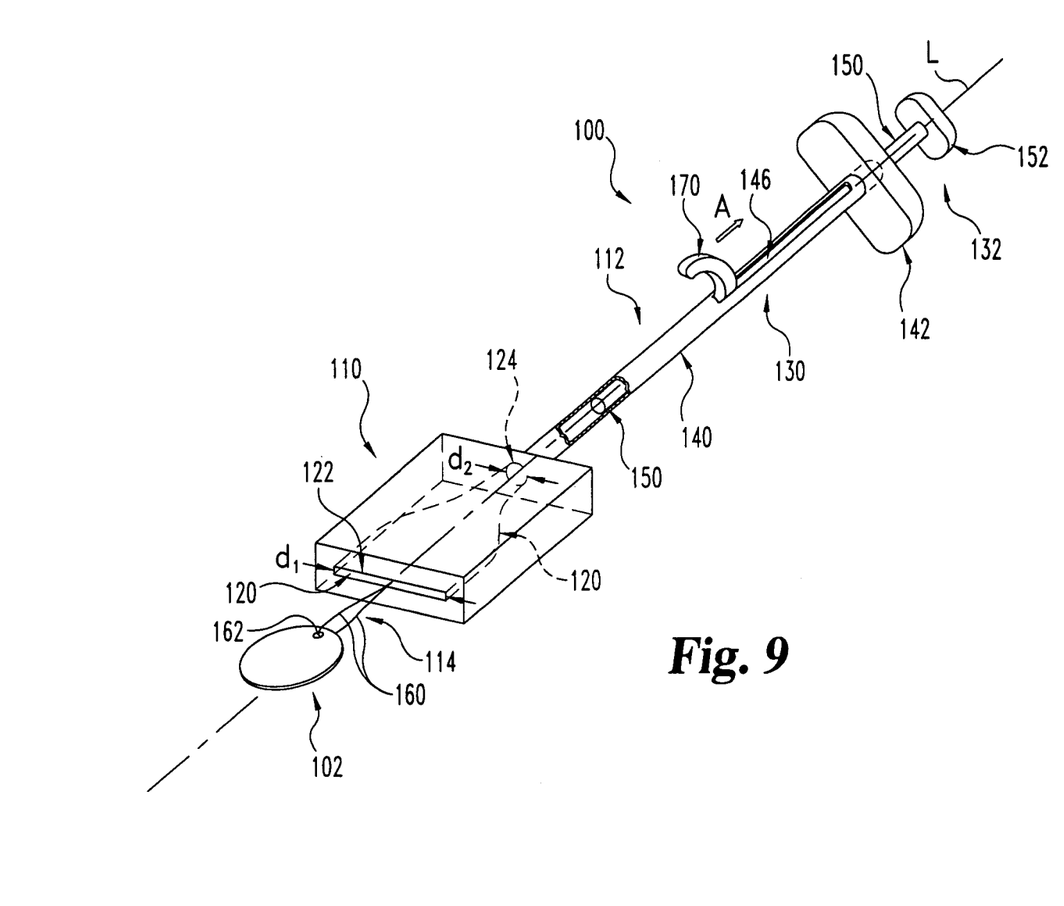
FIG. 9 is a perspective view of an instrument according to another form of the present invention for delivering an implant into a vertebral space.

Referring to FIG. 9, shown therein is a delivery instrument 100 according to another form of the present invention. As will be discussed in further detail below, the delivery instrument 100 is configured to deliver an implant 102 into an anatomical space, such as, for example, a vertebral space. In one embodiment, the delivery instrument 100 is configured to deliver the implant 102 into an intervertebral disc space between adjacent vertebral bodies. However, it should be understood that the delivery instrument 100 may also be used in association with other portions of the spine or in association with portions of the anatomy outside of the spine.

The delivery instrument 100 extends along a longitudinal axis L and is generally comprised of a die member 110, a delivery member 112, and one or more force application members 114 adapted to displace the implant 102 along the die member 110 and into the delivery member 112. As will be discussed in further detail below, the die member 110 is configured to transition or reshape the implant 102 from an initial configuration to a deformed configuration suitable for insertion into a vertebral space. The deformed configuration of the implant 102 is preferably sized so as to allow insertion of the implant 102 into the vertebral space in a minimally invasive manner. As will also be discussed below in further detail below, the delivery member 112 is configured to receive and selectively retain the implant 102 in the deformed configuration prior to insertion of the implant 102 into the vertebral space. Additionally, in one embodiment of the invention, the die member 110 is releasably coupled to the delivery member 112 so as to allow the die member 110 to be selectively separated or removed from the delivery member 112, the details of which will be discussed below.

In one embodiment of the invention, the die member 110 defines an opening 120 configured to receive the implant 102 and transition the implant 102 from the initial configuration to the deformed configuration. In a further embodiment, the opening 120 comprises a passage extending generally along the longitudinal axis L and including a first portion 122 defining a first transverse dimension $d_1$ and a second portion 124 defining a second transverse dimension $d_2$ that is less than the first transverse dimension $d_1$. In one embodiment of the invention, the second transverse dimension $d_2$ is less than half the first transverse dimension $d_1$. In another embodiment of the invention, the second transverse dimension $d_2$ is less than one-third the first transverse dimension $d_1$. It should be understood, however, that other ratios between the transverse dimensions $d_1$, $d_2$ are also contemplate as falling within the scope of the present invention.

The first passage portion 122 is sized to receive the implant 102 while in an initial configuration having a lateral profile somewhat less than the transverse dimension $d_1$. As the implant 102 is axially displaced along the passage 120 toward the second passage portion 124, the implant 102 is transitioned from the initial configuration toward a deformed configuration having a reduced lateral profile relative to the initial configuration. The passage 120 is preferably inwardly tapered in a transverse direction from the first passage portion 122 toward the second passage portion 124 to facilitate transitioning of the implant 102 from the initial configuration toward the deformed configuration. Once positioned within the second passage portion 124, the implant 102 will have a reduced lateral profile approximately equal to the transverse dimension $d_2$ of the second passage portion 124.

In the illustrated embodiment of the invention, the first passage portion 122 has a slotted configuration defining a substantially rectangular cross-section, while the second passage portion 124 defines a substantially circular cross-section. In this embodiment, the implant 102 initially has a substantially planar configuration suitable for insertion into the rectangular passage portion 122, and is transitioned toward a substantially cylindrical configuration as the implant 102 is displaced along the passage 120 toward the circular passage portion 124. However, it should be understood that the first and second passage portions 122, 124 may be configured to define other types of cross-sections, such as, for example, square, polygonal, oblong and/or elliptical cross-sections, or any other suitable cross-section that would occur to one of skill in the art. Likewise, it should be understood that the implant 102 may correspondingly define non-planar initial configurations and/or non-cylindrical deformed configurations.

In one embodiment of the invention, the delivery member 112 is generally comprised of a retention member 130 configured to receive and retain the implant 102 in the reduced-profile deformed configuration, and a discharge member 132 configured to selectively discharge the implant 102 from the retention member 130 and into a vertebral space. In one embodiment, the retention member 130 includes an outer tube portion 140 and a proximal handle portion 142. The outer tube portion 140 defines an axial cavity or cannula passage 142 adapted to receive the implant 102 when in the deformed configuration and to selectively retain the implant 102 in the deformed configuration prior to insertion into the vertebral space. The outer tube portion 140 also defines an axially extending slot 146, the purpose of which will be discussed below. In one embodiment, the discharge member 132 comprises an inner rod portion 150 and a proximal handle portion 152. The inner rod portion 150 is adapted for axial displacement along the cavity 144 in the outer tube 140 so as to engage the implant 102 to discharge the implant 102 from the outer tube 140 and into the vertebral space.

As discussed above, in one embodiment of the invention, the die member 110 is releasably coupled to the delivery member 112 so as to allow the die member 110 to be selectively separated or removed from the delivery member 112 subsequent to the loading of the implant 102 into the cavity 144 in the delivery member 112. In this manner, the implant 102 may be discharged from the cavity 144 adjacent the unobstructed distal end portion of the delivery member 112 and into the vertebral space. Following its removal, the empty die member 110 may be discarded. Alternatively, the die member 110 may be sterilized for reuse.

Figure 16:
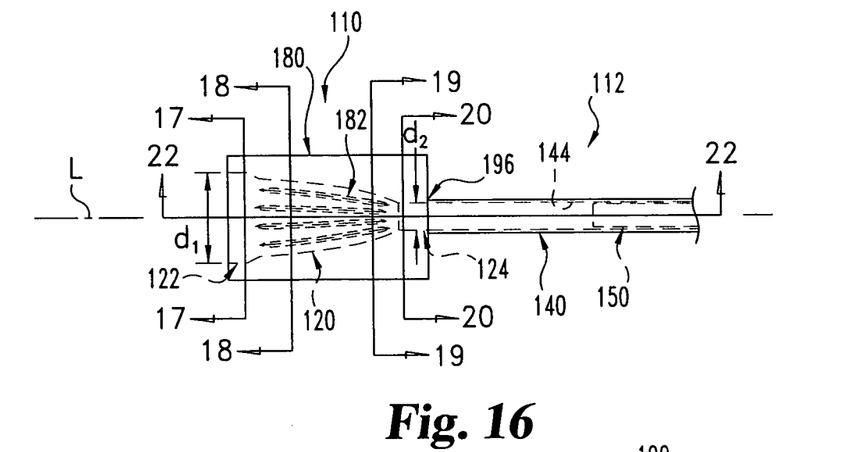
FIG. 16 is a top plan view of the instrument illustrated in FIG. 9.
Figure 17:
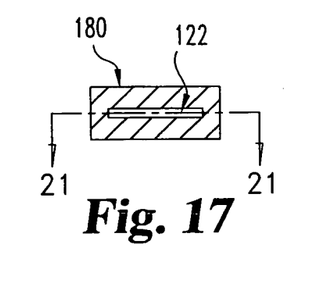
FIG. 17 is a cross-sectional view of the instrument illustrated in FIG. 16, as taken along line 17-17 of FIG. 16.

In one embodiment of the invention, the delivery member 112 is releasably coupled to the die member 110 by a frangible region 196 (FIG. 16) configured to allow the die member 110 to be selectively snapped off or broken away from the delivery member 112. In a specific embodiment, the frangible region 196 comprises a region of reduced strength, such as, for example, a region of reduced wall thickness. It should be understood, however, that the instrument 100 may be equipped with other features to allow the die member 110 to be selectively separated or removed from the delivery member 112. For example, in another embodiment, the instrument 100 may include a slidable connection between the die member 110 and the delivery member 112, such as, for example, a tongue and groove arrangement, to allow the die member 110 to be selectively removed from the delivery member 112. In a further embodiment, the instrument 100 may include a threaded connection between the die member 110 and the delivery member 112 to provide for selective removal of the die member 110. In another embodiment, the die member 110 and the delivery member 112 are integrally formed as a single-piece structure. However, it should be understood that the die member 110 and the delivery member 112 may alternatively be formed as separate elements that may be subsequently attached together to form an integral structure.

In one embodiment of the invention, the force application member 114 is comprised of one or more filament or strand members 160 engaged to the implant 102. In the illustrated embodiment, the filament member 160 comprises a suture that is looped through an aperture 162 extending through the implant 102. However, it should be understood that other types and configurations of force application members 114 are also contemplated as falling within the scope of the present invention. Although the illustrated embodiment of the invention includes a single filament member or suture loop 160, it should be understood that multiple filament members may be used, such as, for example, as shown in FIG. 1 and described above with regard to the implant 50.

In one embodiment of the invention, the suture loop 160 extends through the passage 120 in the die member 110, along the cannula passage 144 in the delivery member 112, and out the axial slot 146 formed along the delivery member 112. A hook member 170 is attached to the suture loop 160 adjacent the axial slot 146. As should be appreciated, pulling the hook member 170 in the direction of arrow A will tension the suture loop 160 and will correspondingly displace the implant 102 through the die member 110 to transition the implant 102 from the initial configuration toward the deformed configuration. Following transitioning of the implant 102 to the deformed configuration, the suture loop 160 may be removed from the implant 102 by simply cutting one side of the suture loop 160 and pulling the severed portion of the suture loop through the aperture 162 in the implant 102. Although the illustrated embodiment of the invention utilizes filaments or sutures 160 to draw the implant 102 through the die member 110, it should be understood that other types and configurations of force application members 114 are also contemplated. For example, the force application member 114 may be configured to displace the implant 102 through the folding member 110 via an axial pushing force and/or a rotational force.

Figures 10, 11, 12, 14:
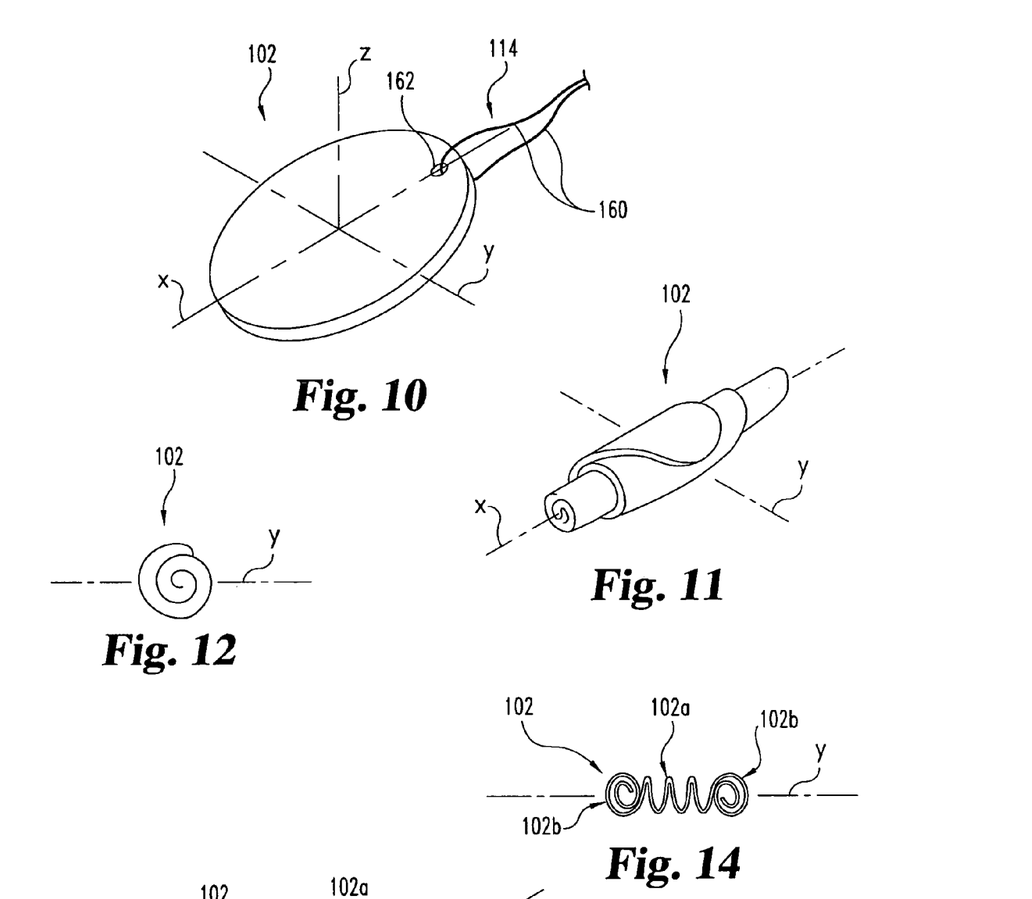
FIG. 10 is a perspective view of an implant according to one form of the present invention suitable for delivery into a vertebral space using the instrument illustrated in FIG. 9.
FIG. 11 is a perspective view of the implant illustrated in FIG. 10, as shown in a rolled configuration.
FIG. 12 is an end elevational view of the rolled implant illustrated in FIG. 11.
FIG. 14 is an end elevational view of the implant illustrated in FIG. 10, as shown in a partially rolled, partially folded configuration.

Referring to FIG. 10, shown therein is the implant 102 according to one form of the present invention. In one embodiment, the implant 102 is a spinal implant suitable for insertion into a vertebral space. In a specific embodiment, the implant 102 is a prosthetic or artificial nucleus suitable for insertion into an intervertebral disc space to replace at least a portion of the nucleus pulposus of a natural disc to restore bio-mechanical function similar that of the natural disc. However, it should be understood that the implant 102 may be used to replace other portions of the spine or may alternatively be used in association with other portions of the anatomy outside of the spine.

The implant 102 is preferably formed of relatively thin wafer of biologically compatible material. In one embodiment of the invention, the implant 102 has a substantially planar, disc-like configuration while in an initial configuration, extending generally along a plane defined by axis x and axis y. Although the implant 102 is illustrated as having a generally circular shape, other shapes and configurations of the implant 102 are also contemplated, including oval-shaped, elliptical-shaped, kidney-shaped, rectangular-shaped or polygonal-shaped implants, or any other shape that would occur to one of skill in the art. In a preferred embodiment of the invention, the implant 102 is formed of a flexibly deformable material to facilitate transitioning from the initial configuration to a reduced-profile deformed configuration. In a further embodiment of the invention, the implant 102 is formed of an elastically deformable material to facilitate transitioning of the implant 102 from the initial configuration to an elastically deformed configuration and reformation back toward the initial configuration.

Figure 13:
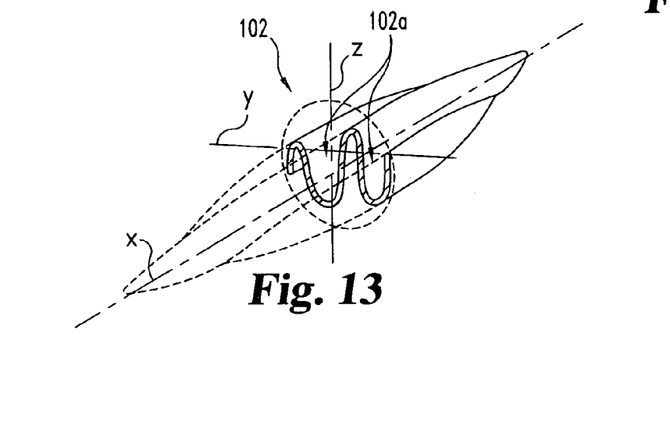
FIG. 13 is a perspective view of the implant illustrated in FIG. 10, as shown in a folded configuration.

As illustrated in FIGS. 11-14, the implant 102 is capable of being transitioned from the planar configuration illustrated in FIG. 10 to a variety of deformed configurations. For example, as shown in FIGS. 11 and 12, the implant 102 may be deformed into a rolled or curled configuration, thereby reducing the lateral dimension or profile of the implant 102 along axis y relative to the initial configuration shown in FIG. 10. As shown in FIG. 13, the implant 102 may also be deformed into a folded configuration defining a number of folded portions 102a extending generally along axis z, also resulting in a reduction in the lateral dimension or profile of the implant 102 along axis y. Additionally, as shown in FIG. 14, the implant 102 may be deformed into a partially rolled, partially folded configuration defining a number of folded portions 102a and a number of rolled or curled portions 102b, likewise resulting in a reduction in the lateral dimension or profile of the implant 102 along axis y. It should be understood that the implant 102 may be transitioned into other deformed configurations in addition to or in combination with the deformed configurations specifically described and illustrated herein. Additionally, it should be appreciated that the implant 102 may be transitioned from the planar configuration illustrated in FIG. 10 to any non-planar configuration.

Figure 15:
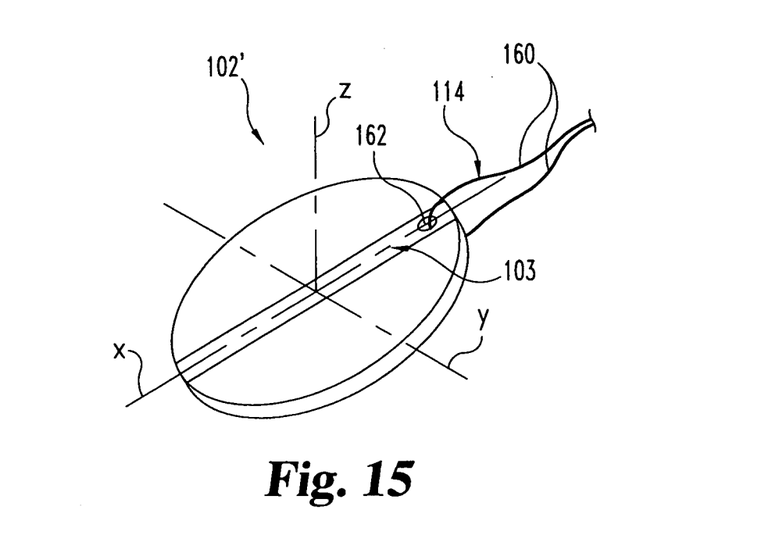
FIG. 15 is a perspective view of an implant according to yet another form of the present invention.

Referring to FIG. 15, shown therein is an implant 102' according to another embodiment of the present invention. The implant 102' is configured similar to the implant 102, preferably having an initial substantially planar configuration extending generally along a plane defined by axis x and axis y. However, the implant 102' includes one or more features that function to permit, assist, facilitate, direct, aid in, and/or control deformation and/or reformation of the implant 102.

In one embodiment of the invention, the implant 102' includes one or more elastic members or struts 103 extending generally along axis x to facilitate reformation of the implant 102 from a deformed configuration back toward its initial configuration (e.g., reformation from a rolled, curled, or folded configuration back toward a substantially planar configuration). In a further embodiment, the elastic struts 103 are formed of a superelastic material to further aid in reformation of the implant 102 from a deformed configuration back toward its initial configuration. In a specific embodiment, the struts 103 are formed of a shape-memory material to incorporate memory characteristics into the implant 102' to facilitate reformation back from the deformed configuration back toward a "memorized" initial configuration. Although the illustrated embodiment of the implant 102' depicts a particular arrangement and orientation of the elastic strut 103, it should be understood that other arrangements are also contemplated, including embodiments having one or more elastic struts 103 alternatively arranged transverse to axis x so as, for example, to extend along axis y.

Additionally, it should be understood that other features may be incorporated into the implants 102, 102' to facilitate or assist in deformation and/or reformation. For example, as discussed above with regard to the implants 90 and 90', the implant 102' may include one or more ribbed sections and/or one or more rigid, semi-rigid or flexible portions incorporated into, encased within, or attached to the remainder of the implant. Additionally, portions of the implants 102, 102' may be formed of a material having a particular material weave or grain pattern to direct deformation and/or reformation in a particular direction and/or orientation. Further, the implants 102, 102' may define a number of openings and/or notches or grooves to provide a degree of control over the deformation and/or reformation. Additionally, the implants 102, 102' may be formed as composites comprising two or more different materials to regulate deformation and/or reformation in a particular direction and/or orientation.

It should also be appreciated that the implants 102 and 102' may be packaged in an initial, substantially planar configuration to provide for convenient packaging, handling, shipping, storage and assembly. Additionally, by providing the implants 102, 102' with an initial, substantially planar configuration that is subsequently transitioned to a deformed configuration immediately prior to insertion into the intervertebral disc space, the implants 102, 102' are less likely to develop a bias or shape memory as otherwise might occur if the implants were prepackaged in a delivery member for an extended period of time in a deformed configuration, such as might be apparent during shipping and storage.

Referring collectively to FIGS. 16-21, shown therein are further details regarding the die member 110. As discussed above, the die member 110 defines an axially-extending passage 120 including a first portion 122 having a substantially rectangular cross-section defining a transverse dimension $d_1$ and a second portion 124 having a substantially cylindrical cross-section defining a reduced transverse dimension $d_2$. In one embodiment of the invention, the die member 110 is comprised of a folding block or container 180 defining the passage 120 and a number of folding elements or guides 182 extending axially along at least a portion of the passage 120. The folding elements 182 act to initiate and facilitate transitioning of the implant 102 from the initial configuration toward a deformed configuration (FIGS. 22-24) to accommodate loading of the implant 102 into the cavity 144 of the delivery member 112. Although the folding elements 182 are illustrated as being defined entirely by the die member 110, it should be understood that the folding elements 182 may be partially defined by the delivery member 112 (e.g., extending into the cavity 144 of the delivery tube 140).

Figure 18:
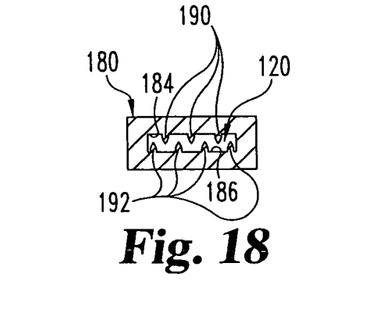
FIG. 18 is a cross-sectional view of the instrument illustrated in FIG. 16, as taken along line 18-18 of FIG. 16.
Figure 19:
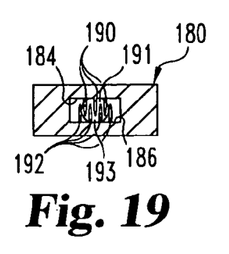
FIG. 19 is a cross-sectional view of the instrument illustrated in FIG. 16, as taken along line 19-19 of FIG. 16.
Figure 20:
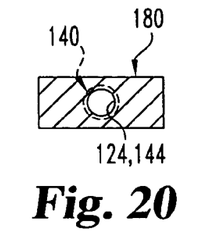
FIG. 20 is a cross-sectional view of the instrument illustrated in FIG. 16, as taken along line 20-20 of FIG. 16, with the implant disposed within a delivery portion of the instrument.
Figure 21:
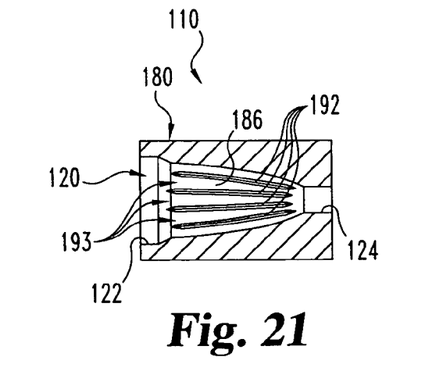
FIG. 21 is a cross-sectional view of the instrument illustrated in FIG. 16, as taken along line 21-21 of FIG. 17.

As illustrated in FIGS. 18 and 19, the passage 120 is bound by an upper surface 184 and an opposite lower surface 186. In one embodiment of the invention, the folding elements 182 include a number of upper protrusions 190 extending from the upper surface 184 and a number of grooves or notches 191 defined between adjacent pairs of the protrusions 190. Similarly, the folding elements 182 include a number of lower protrusions 192 extending from the lower surface 186 and a number of grooves or notches 193 defined between adjacent pairs of the protrusions 192. In one embodiment, the upper protrusions 190 are transversely offset relative to the lower protrusions 192 such that the upper protrusions 190 are disposed opposite the lower grooves 193 and the lower protrusions 192 are disposed opposite the upper grooves 191. As shown in FIG. 21, the folding elements 182 are preferably inwardly tapered relative to one another in a transverse direction from the first passage portion 122 toward the second passage portion 124 to facilitate folding of the implant 102. In a specific embodiment of the invention, at least the distal end portions of the upper and lower protrusions 190, 192 have a triangular configuration to further assist in the folding of the implant 102. It should be understood, however, that other shapes and configurations are also contemplated.

Figure 22:
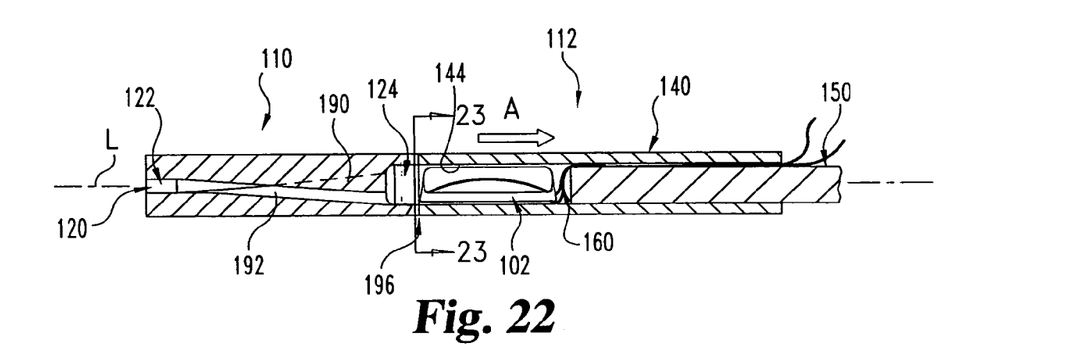
FIG. 22 is a cross-sectional view of the instrument illustrated in FIG. 16, as taken along line 22-22 of FIG. 16.
Figure 23:
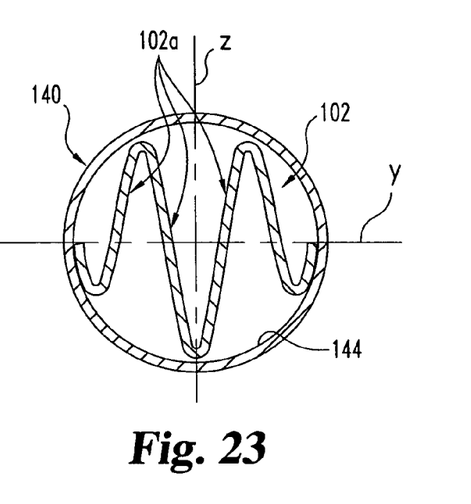
FIG. 23 is a cross-sectional view of the instrument illustrated in FIG. 22, as taken along line 23-23 of FIG. 22.

Referring to FIGS. 22 and 23, shown therein is the implant 102 positioned within the cavity 144 of the delivery tube 140 in a deformed/folded configuration. The implant 102 is initially disposed outside of the die member 110 in a substantially planar initial configuration (FIG. 9). As discussed above, pulling the suture loop 160 in the direction of arrow A via the hook member 170 exerts an axial pulling force onto the implant 102 which in turn draws the implant 102 through the die member 110 and into the distal end portion of the delivery member 112. More specifically, axial displacement of the implant 102 through the passage 120 and across the folding elements 182 (e.g., protrusions 190, 192 and grooves 191, 193) transitions the implant 102 from the initial planar configuration toward the substantially cylindrical deformed configuration (FIG. 23) and loads the deformed implant 102 into the cavity 144 of the delivery member 112.

As illustrated in FIG. 23, the deformed/folded configuration of the implant 102 has a reduced lateral dimension or profile along axis y relative to the initial configuration of the implant 102 illustrated in FIG. 9. Once loaded into the cavity 144, the delivery tube 140 serves to temporarily house and selectively maintain the implant 102 in the deformed/folded configuration. As discussed above, the suture loop 160 may be disconnected from the implant 102 by simply cutting one side of the suture loop and pulling the severed suture loop through the aperture 162 in the implant 102. It should be appreciated that the suture loop 160 may be removed after the implant 102 is loaded into the delivery tube 140 or subsequent to delivery of the implant 102 into the vertebral space. Once the implant 102 is folded into the reduced-profile configuration and loaded into the delivery member 112, the die member 110 is selectively removed from the delivery member 112. As discussed above, in the illustrated embodiment of the invention, the die member 110 is broken away from or snapped off from the delivery member 112 at the frangible region 196, thereby providing the delivery tube 140 with an unobstructed, open distal end.

Figure 24:
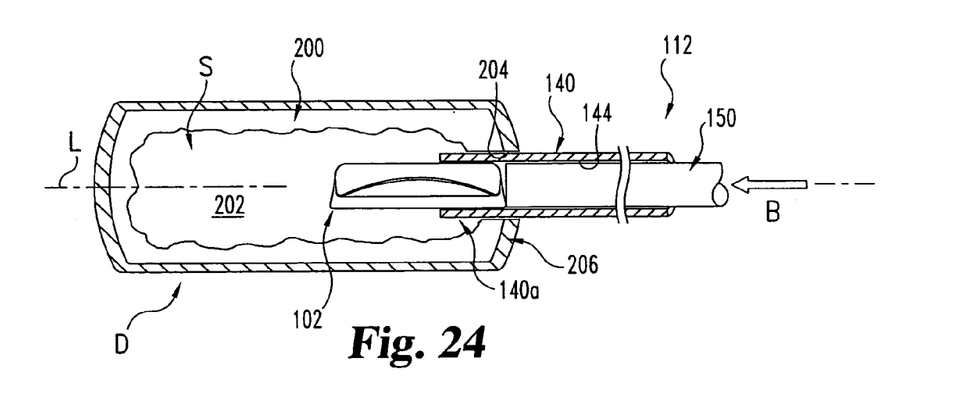
FIG. 24 is a partial cross-sectional view of the instrument illustrated in FIG. 9, as shown delivering the implant into an intervertebral disc space.

Referring to FIG. 24, shown therein is a distal end portion 140a of the delivery tube 140 inserted into an intervertebral disc D for delivery of the implant 102 into the intervertebral disc space S. In one embodiment of the invention, prior to insertion of the delivery tube 140 into the disc space S, at least a portion of the nucleus pulposus 200 is removed to form a hollowed out chamber 202, the details of which would be known to one of skill in the art. Additionally, a small access portal or opening 204 is formed through the annulus fibrosus 206 in communication with the hollowed-out chamber 202. The access opening 204 is preferably only slightly larger than the outer cross-section of the delivery tube 140 so as to permit insertion of the distal end portion 140a of the delivery tube 140 into the disc space S in a minimally invasive manner.

Following insertion of the distal end portion 140a through the access opening 204 and into the disc space chamber 202, the inner rod portion 150 of the delivery member 112 is axially displaced along the tube cavity 144 in the direction of arrow B to engage the implant 102 and discharge the implant 102 from the delivery tube 140 and into the disc space chamber 202. Once the implant 102 is delivered into the disc space chamber 202, the implant 102 will reform or unfold back toward its initial, substantially planar configuration (FIG. 9). The position and/or orientation of the implant 102 may be adjusted within the disc space chamber 202, or possibly removed from the disc space chamber 202, by tensioning the suture loop 160 if still connected to the implant 102. The distal end portion 140a of the delivery tube 140 may also be used to adjust the position and/or orientation of the implant 102 within the disc space chamber 202.

In a further embodiment of the invention, the implant 102 may be configured to change shape due to swelling, hydration, expansion, reaction, or by other means subsequent to insertion into the intervertebral disc space so as to increase the height of the implant 102 along axis z (FIG. 10) to substantially correspond to the height of the disc space chamber 202. Similarly, the implant 102 may also be configured to increase in size along axis x and/or axis y subsequent to insertion into the intervertebral disc space to substantially correspond to the inner perimeter of the disc space chamber 202. Further details regarding these and other expansion features and characteristics are disclosed in U.S. patent application Ser. No. 09/559,899, filed Apr. 26, 2000, the contents of which have been incorporated herein by reference.

As should now be appreciated, prior to being transitioned to its deformed configuration via the delivery instrument 100, the implant 102 has at least one dimension (e.g., a y dimension) that is larger than the maximum dimension of the insertion portal through with the implant 102 is required to pass. Accordingly, one advantage provided by the present invention is that delivery of the implant 102 into the intervertebral disc space S may be accomplished in a minimally invasive manner via a relatively small insertion portal or opening, thereby minimizing trauma to and/or weakening of adjacent tissue, such as, for example, the annulus fibrosus or the remaining portion of the nucleus pulposus.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for delivering a spinal implant into a vertebral space, comprising:
    providing a deformable spinal implant;
    providing a die member defining a passage extending along a longitudinal axis and including a first portion sized to receive the implant while in an initial configuration, wherein the passage is bound by a first surface and an oppositely facing second surface and the die member includes a number of projections extending transversely from at least one of the first and second surfaces and into the passage, wherein the first portion of the passage defines a first transverse width dimension inwardly tapering to a second transverse width defined by a second portion of the passage, the first portion of the passage defining a first transverse height dimension outwardly tapering to a second transverse height dimension defined by the second portion;
    providing a delivery member defining a cavity and removably engaged with the die member with the cavity generally aligned the passage;
    inserting the implant into the opening in the die member;
    displacing the implant relative to the die member and drawing the implant over the number of projections;
    transitioning the implant from the initial configuration to a deformed configuration in response to the drawing of the implant over the number of projections, the deformed configuration having a reduced lateral profile relative to the initial configuration; and
    discharging the implant from the die member and into the cavity of the delivery member while in the deformed configuration and selectively retaining the implant in the deformed configuration in the cavity;
    selectively removing the delivery member from the die member; and
    discharging the implant from the cavity of the delivery member and into the vertebral space while in the deformed configuration.

2. The method of claim 1, wherein the number of projections comprise folding elements that facilitate transitioning of the implant from the initial configuration to a folded configuration; and
    wherein a first series of the folding elements extend from the first surface of the passage, and a second series of the folding elements extend from the second surface of the passage.

3. The method of claim 1, further comprising inserting a distal end of the delivery member into the vertebral space prior to the discharging of the implant into the vertebral space.

4. The method of claim 1, wherein the implant is formed of a resilient material configured to resiliently transition the implant from the deformed configuration back toward the initial configuration subsequent to insertion into the vertebral space.

5. The method of claim 1, wherein the number of projections each have a triangular configuration.

6. The method of claim 1, wherein the first transverse width dimension comprises a first overall transverse width dimension of the first portion of the passage adjacent a first end of the die member, and the second transverse width dimension comprises a second overall transverse width dimension of the second portion of the passage adjacent an opposite second end of the die member; and wherein the first transverse height dimension comprises a first overall transverse height dimension of the first portion of the passage adjacent die first end of the die member, and the second transverse height dimension comprises a second overall transverse height dimension of the second portion of the passage adjacent the opposite second end of the die member.

7. The method of claim 6, wherein the first overall transverse width dimension comprises a maximum overall transverse width dimension of the passage, and the second transverse width dimension comprises a minimum overall transverse width dimension of the passage; and wherein the first transverse height dimension comprises a minimum overall transverse height dimension of the passage, and the second transverse height dimension comprises a maximum overall transverse height dimension of the passage.

8. A method for delivering a spinal implant into a vertebral space comprising:

providing a deformable spinal implant;

providing a die member defining a passage extending along a longitudinal axis and haying an inlet opening and an outlet opening, the inlet opening having an inlet width dimension and an inlet height dimension, the passage inwardly tapering along the longitudinal axis to provide the outlet opening with a reduced outlet width dimension relative to the inlet width dimension, the passage outwardly tapering along the longitudinal axis to provide the outlet opening with an increased outlet height dimension relative to the inlet height dimension;

providing a delivery member defining a cavity and removably engaged with the die member with the cavity generally aligned with the outlet opening;

inserting the implant into the inlet opening while the implant is in an initial configuration;

displacing the implant from the inlet opening toward the outlet opening to transition the implant from the initial configuration to a deformed configuration having a reduced width profile relative to the initial configuration and an increased height profile relative to the initial configuration;

discharging the implant from the outlet opening of the die member and into the cavity of the delivery member while in the deformed configuration and selectively retaining the implant in the deformed configuration in the cavity;

selectively removing the delivery member from the die member; and discharging the implant from the cavity of the delivery member and into the vertebral space while in the deformed configuration.

9. The method of claim 8, further comprising inserting a distal end of the delivery member into the vertebral space prior to the discharging of the implant into the vertebral space.

10. The method of claim 8, wherein the implant is formed of a resilient material configured to resiliently transition the implant from the deformed configuration back toward the initial configuration subsequent to insertion of the implant into the vertebral space.

11. The method of claim 8, wherein the passage is bound by first surface and an oppositely facing second surface and the die member includes a number of folding projections extending transversely from at least one of the first and second surfaces and into the passage; and wherein the displacing of the implant along the passage draws the implant over the number of folding projections to transition the implant from the initial configuration to a folded configuration.

12. The method of claim 8, wherein the inlet width dimension comprises an overall inlet width dimension of the inlet opening of the passage adjacent a first end of the die member, and the outlet is dimension comprises an overall outlet width dimension of the outlet opening of the passage adjacent an opposite second end of the die member; and wherein the inlet height dimension comprises an overall inlet height dimension of the inlet opening of the passage adjacent the first end of the die member, and the outlet height dimension comprises an overall outlet height dimension of the outlet opening of the passage adjacent the opposite second end of the die member.

13. The method of claim 12, wherein the overall inlet width dimension comprises as maximum overall width dimension of the passage, and the overall outlet width dimension of the passage comprises a minimum overall width dimension of the passage; and wherein the overall inlet height dimension comprises a minimum overall height dimension of the passage, and the overall outlet height dimension of the passage comprises a maximum overall height dimension of the passage.

14. A method for delivering a spinal implant into a vertebral space, comprising:

providing a deformable spinal implant transitionable between an initial configuration and a deformed configuration;

providing a die member including a passage extending along an axis, the passage including a first portion defining a first transverse width dimension inwardly tapering to a second portion defining a second transverse width dimension less than the first transverse width dimension, the first portion defining a first transverse height dimension outwardly tapering to the second portion which defines a second transverse height dimension greater than the first transverse height dimension, the first portion of the passage sized to receive the implant while in the initial configuration;

providing a delivery member defining a cavity and removably engaged with the die member with the cavity generally aligned with the second portion of the passage;

positioning the implant into the first portion of the passage while in the initial configuration;

displacing the implant along the passage in an axial direction toward the second portion of the passage and transitioning the implant from the initial configuration toward the deformed configuration, the deformed configuration of the implant having a reduced width profile relative to the initial configuration and an increased height profile relative to the initial configuration;

discharging the implant from second portion of the passage and into the cavity of the delivery member while in the deformed configuration and selectively retaining the implant in the deformed configuration in the cavity;

selectively removing the delivery member from the die member; and discharging the implant from the cavity of the delivery member and into the vertebral space while in the deformed configuration.

15. The method of claim 14, further comprising inserting a distal end of the delivery member into the vertebral space prior to the discharging of the implant into the vertebral space.

16. The method of claim 14, wherein the implant is formed of a resilient material configured to resiliently transition the implant from the deformed configuration back toward the initial configuration subsequent to insertion into the vertebral space.

17. The method of claim 14, wherein the passage is bound by a first surface and an oppositely facing second surface and the die member includes a number of folding projections extending transversely from at least one of the first and second surfaces and into the passage; and wherein the displacing of the implant along the passage draws the implant over the number of folding projections to transition the implant from the initial configuration to a folded configuration.

18. The method of claim 14, wherein the first transverse width dimension comprises a first overall transverse width dimension of the first portion of the passage adjacent a first end of the die member, and the second transverse width dimension comprises a second overall transverse width dimension of the second portion of the passage adjacent an opposite second end of the die member; and wherein the first transverse height dimension comprises a first overall transverse height dimension of the first portion of the passage adjacent the first end of the die member, and the second transverse height dimension comprises a second overall transverse height dimension of the second portion of the passage adjacent the opposite second end of the die member.

19. The method of claim 18, wherein the first overall transverse width dimension comprises a maximum overall transverse width dimension of the passage, and the second transverse width dimension comprises a minimum overall transverse width dimension of the passage; and wherein the first transverse height dimension comprises a minimum overall transverse; height dimension of the passage, and the second transverse height dimension comprises a maximum overall transverse height dimension of the passage.

* * * * *